US009009075B2

(12) United States Patent
Dominick et al.

(10) Patent No.: US 9,009,075 B2
(45) Date of Patent: Apr. 14, 2015

(54) TRANSFER SYSTEM FOR SECURITY-CRITICAL MEDICAL IMAGE CONTENTS (71) Applicant: Siemens Aktiengesellschaft, Munich (DE)

(72) Inventors: Lutz Dominick, Eggolsheim (DE); Hans-Martin Von Stockhausen, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 14/053,662

(22) Filed: Oct. 15, 2013

(65) Prior Publication Data
US 2014/0214683 A1 Jul. 31, 2014

(30) Foreign Application Priority Data

Jan. 28, 2013 (EP) .................................... 13152855

(51) Int. Cl.
*G06F 21/00* (2013.01)
*G06F 19/00* (2011.01)
*G06F 21/62* (2013.01)
G06F 9/54 (2006.01)
G06Q 50/24 (2012.01)
H04L 29/06 (2006.01)

(52) U.S. Cl.
CPC .............. *G06F 19/321* (2013.01); *G06F 9/543* (2013.01); *G06Q 50/24* (2013.01); *H04L 63/0428* (2013.01); *G06F 21/6254* (2013.01); *G06F 2221/2105* (2013.01); *G06F 19/322* (2013.01)

(58) Field of Classification Search
None
See application file for complete search history.

(56) References Cited

U.S. PATENT DOCUMENTS

| 5,964,834 | A | 10/1999 | Crutcher | |
|---|---|---|---|---|
| 6,735,347 | B1 * | 5/2004 | Bates et al. | 382/282 |
| 7,950,066 | B1 * | 5/2011 | Zuili | 726/33 |
| 8,555,187 | B2 * | 10/2013 | Margolin | 715/770 |

(Continued)

OTHER PUBLICATIONS

"Digital Imaging and Communications in Medicine (DICOM) Part 15: Security and System Management Profiles"; National Electrical Manufacturers Association; pp. 1-133; XP055067393; abgerufen im Internet: http://medical.nema.org/Dicom/2011/11_15pu.pdf; 2011; Jan. 1, 2011.

(Continued)

*Primary Examiner* — John Hayes
*Assistant Examiner* — Jason Fenstermacher
(74) *Attorney, Agent, or Firm* — Harness, Dickey & Pierce, P.L.C.

(57) ABSTRACT

A transfer method, a system and a product are disclosed for transferring security-critical medical image data records with PHI sections from a source application to a destination application. In an embodiment, the method accesses a PKI infrastructure that provides a user-specific key for each user. Following detection of a copy command for at least one image data record in the source application, a data convolute is produced, including an anonymized and an encrypted image data record, which are forwarded to a trader module and/or a memory module. After a pasted command is detected, the key is used to access the clipboard and/or the memory module in order to decrypt the image data record from the encrypted image data record and to paste it (for a secure destination application), and/or to access the anonymized image data record and to paste it (for a nonsecure destination application).

15 Claims, 3 Drawing Sheets

(56) References Cited

U.S. PATENT DOCUMENTS

2008/0301805 A1    12/2008   Bharara et al.
2010/0313274 A1    12/2010   Crucs
2011/0110568 A1*   5/2011    Vesper et al. ................ 382/128

OTHER PUBLICATIONS

European Search Report for European patent application 13152855.6 dated Jun. 20, 2013.

* cited by examiner

FIG 1

TRANSFER SYSTEM FOR SECURITY-CRITICAL MEDICAL IMAGE CONTENTS

PRIORITY STATEMENT

The present application hereby claims priority under 35 U.S.C. §119 to European patent application number EP 131 52855.6 filed Jan. 28, 2013, the entire contents of which are hereby incorporated herein by reference.

FIELD

At least one embodiment of the present invention generally relates to the fields of medical engineering and information technology and relates particularly to a method for copying security-critical image contents and possibly pasting them in the same or in a different application, which may also be implemented on a different application appliance.

BACKGROUND

Particularly in the medical context, the handling is effected increasingly by way of data processing devices and on the computer basis. By way of example, a large number of different applications are available for performing surgical, robot-controlled interventions, for examination, for data archiving, etc. In the area of imaging medicine, it is necessary for the image data acquired to be processed and stored. To this end, it is useful to copy individual image contents or whole images from an application and to paste them again at a different location.

In the prior art, this is accomplished by resorting to short-term memories, what are known as clipboards, that can be used to store content to be transferred so that it can be accessed later. The clipboard functionality can therefore be used for executing copy and paste commands. As described in U.S. Pat. No. 5,964,834, for example, a respective clipboard may be associated with a processor in a wired computer network in this case.

In the clinical context, mobile application appliances (laptops, PDAs, mobile sensor appliances, such as blood pressure/sugar measuring appliances etc.) are also used to an increasing extent. The copy and paste functionality also needs to be available for mobile application appliances.

Furthermore, it is necessary to take into account that the medical image data records usually comprise security-critical content that needs to be processed and treated with access protection. It is thus necessary to ensure that patient-identifying details (e.g. name, age, sex, place of residence, etc.) do not cross the boundaries of the respective access-protected environment in combination with image data or image data segments. These access-protected contents are called "protected health information (PHI)".

For security reasons, it is therefore not possible for the standard useful copy and paste functionality, which is known from word processing programs, for example, also to be made available in the area of clinical medicine, since these techniques do not allow the medical data protection criteria to be observed.

In the prior art, it was therefore customary to anonymize the image contents and to store the generated anonymized image data records and also to make them available outside the application or outside the workflow.

SUMMARY

The inventors have discovered that provision of a copy and paste functionality for PHI data records that satisfies the security criteria is not known to date.

Furthermore, they believe that it should also be possible for image contents to be transferred beyond machine boundaries and application boundaries.

At least one embodiment of the invention is directed to providing a way for implementing a copy and paste functionality that allows PHI contents also to be stored and readily accessible beyond workflow and/or machine boundaries, as a result of which the security criteria for the medical area are satisfied.

At least one embodiment of the invention is directed to a computer-implemented method, a computer-based transfer system and/or to a computer program product.

Features, advantages and/or alternative embodiments that are mentioned in this context can similarly also be transferred to the other claimed subjects, and vice versa. In other words, the transfer system or the computer program product can also be developed with the features that are described or claimed in connection with the method. In this case, the corresponding functional features of the method are formed by appropriate object-based computer-implemented modules, particularly microprocessor modules in the system. The transfer system and the method can also be integrated as embedded systems in the acquisition installation or in a medical appliance (e.g. in an imaging acquisition appliance, MRT, CT, US, PET, etc.).

According to one embodiment of the invention, a computer-based method is disclosed for providing a transfer function for security-critical medical data records, particularly image data records, with PHI sections from a source application to a destination application, wherein the method can simultaneously serve destination applications that are recognized as secure and destination applications that are recognized as nonsecure and wherein the method accesses a PKI infrastructure that provides a user-specific key for each user, the method comprising:

following detection of a copy command for at least one image data record in the source application: an anonymized image data record is produced and the image data record and the anonymized image data record are forwarded to a trader module the respective key is detected and at least two data convolutes for the image data record, comprising the anonymized image data record and an encrypted image data record, are created, wherein the encrypted image data record is produced by virtue of the image data being encrypted using the detected key and hence being in cipher at least the anonymized image data record is forwarded to a clipboard and at least the encrypted image data record is forwarded to a memory module for storing an association relation for a key and at least one image data record associated with the respective key from the data convolute following detection of a paste command for at least one image data record in the destination application: the key is detected and it is automatically detected whether the destination application is registered as a secured application or is a nonsecure application if the destination application is a nonsecure application: the destination application accesses the clipboard in order to access the anonymized image data record associated with the detected key and to present on the destination application if the destination application is a secure application: the paste command from the destination application is forwarded to the trader, wherein the trader uses the detected key to access the memory module in order to access the encrypted image data record associated with the respective key and to decrypt it using the key and to provide the decrypted image data record on the destination application.

Furthermore, it is possible for individual sections of the method described above to be produced as individual saleable units and for the remaining sections of the method to be produced as other saleable units. Hence, the method according to an embodiment of the invention can be executed as a distributed system on different computer-based entities (e.g. client-server entities). By way of example, it is thus possible for the trader module for its part to comprise different submodules that are implemented partly on the source application, partly on the destination application and/or partly on other computer-based entities.

Furthermore, an embodiment is directed to a computer program product.

Furthermore, an embodiment is directed to a computer program that comprises computer instructions. The computer instructions may be stored directly on a memory in a computer or can be loaded via a network and comprise commands that the computer can read and that are intended for executing the method described above when the commands are executed on the computer. The computer program may also be stored on a storage medium or it can be downloaded from a server via an appropriate network.

BRIEF DESCRIPTION OF THE DRAWINGS

The detailed description of the figures that follows discusses example embodiments, which are not intended to be restrictive, with the features and further advantages thereof with reference to the drawing, in which.

DETAILED DESCRIPTION OF THE EXAMPLE EMBODIMENTS

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

At least one embodiment of the invention is directed to providing a way for implementing a copy and paste functionality that allows PHI contents also to be stored and readily accessible beyond workflow and/or machine boundaries, as a result of which the security criteria for the medical area are satisfied.

At least one embodiment of the invention is directed to a computer-implemented method, a computer-based transfer system and/or to a computer program product.

Features, advantages and/or alternative embodiments that are mentioned in this context can similarly also be transferred to the other claimed subjects, and vice versa. In other words, the transfer system or the computer program product can also be developed with the features that are described or claimed in connection with the method. In this case, the corresponding functional features of the method are formed by appropriate object-based computer-implemented modules, particularly microprocessor modules in the system. The transfer system and the method can also be integrated as embedded systems in the acquisition installation or in a medical appliance (e.g. in an imaging acquisition appliance, MRT, CT, US, PET, etc.).

According to one embodiment of the invention, a computer-based method is disclosed for providing a transfer function for security-critical medical data records, particularly image data records, with PHI sections from a source application to a destination application, wherein the method can simultaneously serve destination applications that are recognized as secure and destination applications that are recognized as nonsecure and wherein the method accesses a PKI infrastructure that provides a user-specific key for each user, the method comprising:

following detection of a copy command for at least one image data record in the source application: an anonymized image data record is produced and the image data record and the anonymized image data record are forwarded to a trader module the respective key is detected and at least two data convolutes for the image data record, comprising the anonymized image data record and an encrypted image data record, are created, wherein the encrypted image data record is produced by virtue of the image data being encrypted using the detected key and hence being in cipher at least the anonymized image data record is forwarded to a clipboard and at least the encrypted image data record is forwarded to a memory module for storing an association relation for a key and at least one image data record associated with the respective key from the data convolute following detection of a paste command for at least one image data record in the destination application: the key is detected and it is automatically detected whether the destination application is registered as a secured application or is a nonsecure application if the destination application is a nonsecure application: the destination application accesses the clipboard in order to access the anonymized image data record associated with the detected key and to present on the destination application if the destination application is a secure application: the paste command from the destination application is forwarded to the trader, wherein the trader uses the detected key to access the memory module in order to access the encrypted image data record associated with the respective key and to decrypt it using the key and to provide the decrypted image data record on the destination application.

The terminology used in the course of this application is explained in more detail below.

The term "transfer function" comprises a copy and paste functionality for contents, particularly image contents, that are to be protected or that are security-critical. However, the data to be transferred may comprise not only image contents but also other data types, such as text data (meta data for the image data, for example relating to the identity of the patient, or supplementary data for the acquisition appliance, the time of the image acquisition, etc.). The transfer function is not intended to be limited to a particular application, machine or medical workflow, but rather is also intended to be executable across applications, machine boundaries and workflows, while observing the security criteria.

Furthermore, the copy and paste functionality is intended to be able to be applied regardless of whether the destination application on which the image contents to be transferred are intended to be pasted is a secure or nonsecure application. According to embodiments of the invention, the transfer function is provided by a separate entity as an additional operation system module or add-on. It is preferably operating system specific. A fundamental advantage of the transfer function according to embodiments of the invention is that it can be used across manufacturers and can therefore also be used for source and/or destination applications that come from different manufacturers.

The PKI infrastructure (public key infrastructure) is an entity that provides and manages programs/modules for encryption and decryption. Usually, it comprises an association of (public) keys with unique user identities. It can therefore also be in the form of a certification or registration entity.

The image data are medical data records, particularly image data that are captured using imaging appliances (magnetic resonance tomographs, computer tomographs, ultrasound appliances, positron emission tomographs, etc.). In medical image processing, the DICOM protocol (Digital Information and Communications in Medicine) is frequently used for data transfer. Therefore, the image data are preferably in a DICOM format. They comprise not only the image information but also patient-identifying information (name, identity (e.g. unique personal number, etc.), age, sex, supplementary information (such as anamnesis data, diagnoses)). The image data therefore comprise PHI data that are not permitted to leave the secure environment. In an alternative application, the image data may also be PHI data records that are not image data in the actual sense but rather may possibly just be associated therewith (e.g. medical measured values, examination text, etc.), such as text data or data in other formats, however.

The anonymized image data are characterized in that all sections or components that identify the patient have been manipulated or removed from the data record. The anonymized image data can also be de-identified using different measures and then contain no further (patient) identifying pointers. To this end, predeterminable parameters can be eliminated from the data record, generalized, replaced or otherwise manipulated in a specific and decided manner, such as name, geographical data, contact numbers or addresses, including e-mail addresses, security numbers, other ID numbers (e.g. from health insurance cards or bank cards, etc.), biometric data, photos, etc. An alternative measure involves the use of statistical methods that are based on checking the statistical probability of whether the original data can be deduced from the de-identified data record again. Alternatively, it is also possible to employ pseudonymization of the PHI data in this case, this usually having a central association entity between the original PHI data and the pseudonym. In this case, the anonymized image data are visible and universally readable (as plain text)—that is to say are unencrypted.

In contrast to the image data and the anonymized image data, the encrypted image data are characterized in that the image content is no longer available as plain text in readable form, but rather is encrypted and can be decrypted only using an appropriate key. Even if an attacker gains possession of the encrypted image data, he cannot deduce the image data therefrom without the key.

The key is preferably user specific and may be stored either in a central PKI entity or in the appliance itself. In one development of the invention, the PKI key is appliance specific. In that case, the method continues to be limited to the respective appliance. This allows a higher level of security to be observed. Preferably, a symmetric cryptgraphical method is used, as a result of which the key for encryption and decryption matches.

The clipboard is a memory that can be used to temporarily store (buffer) the data records to be transferred, as a result of which the destination application can access them when required in order to paste them at a location to be selected. The clipboard can be provided locally, that is to say on an appliance and operating system specific basis, as a result of which the source application has a clipboard (e.g. Microsoft Windows) and the destination application has an equivalent thereto (possibly different than the clipboard), what is known as a pasteboard (e.g. Apple iPad). Preferably, the clipboard is appliance specific, as a result of which a clipboard is provided for a plurality of applications that are installed on an appliance. Preference is given to single user deployment, in which only one user per appliance or device is actively working at a time. In this case, any number of users can use their devices to participate in the method at the same time.

In a further, example embodiment of the invention, a token is used in order to identify the buffered data records or to render them addressable. This means that it is also possible to execute a multipaste command, in which a plurality of data records can be buffer-stored on the clipboard and in which the destination application can then select the respective relevant data record to be pasted from the set of buffered data records when the paste command is input. This allows the copy and paste functionality to be extended further and made more flexible.

The trader module is an infrastructure component that can preferably be kept available as an executable file or application. Entities of the trader module or modules interacting with the trader module (e.g. in the form of macros) may be formed on the source and/or destination application. These entities or modules can therefore be executed partly on the destination application and partly on the source application. The trader module is preferably implemented as a remote service or as a server-based or cloud-based application that can be accessed via a network (typically via the internet). However, the trader module can also be provided inside the clinic network. Preferably, a trader module is provided for each registered appliance. In this context, "registered" means that the appliance on which the destination application is installed is a secure application and has access to a trader module (in contrast to the nonsecure destination application, which accesses the local clipboard directly rather than the trader). In particular, a trader module is intended to be implemented for the source and destination applications. Alternatively, it is also possible to serve application scenarios in which a trader module is provided for each application.

The memory module is an infrastructure component that is used for buffer-storing (buffering, including repeatedly on a sequential basis) data to be transferred. Preferably, the memory module can be accessed via a network (e.g. cloud-hosted) by the different appliances on which the source and/or destination application is installed.

Secure or Nonsecure Destination Application:

According to one embodiment of the invention, there are two classes of applications provided: secure and nonsecure destination applications. A "secure" destination application is an application in which the PHI contents are intended to be pasted but is situated in the same security environment as the source application and therefore requires no additional security measures for the data transfer. The secure application has a connection to the trader module and "knows" of its own accord that it is "secure". The "nonsecure" destination application is an application in which PHI contents are likewise intended to be pasted but that is not situated in the same security environment as the source application, as a result of which additional security measures for the data transfer are necessary automatically (that is to say without user interaction). The nonsecure application does not have a connection to the trader module and also does not know the distinction between "secure" and "nonsecure". According to one of the invention, it is automatically detected to which of the two classes the destination application belongs. A secure destination application is therefore characterized, inter alia, in that it has a type of service channel, that is to say a secure link to the trader module (subsequently also called trader for short), whereas a nonsecure application (such as Microsoft/Word) does not have this.

In one advantageous development of an embodiment of the invention, it is detected not only whether the application (destination application) is secure or nonsecure but also whether the appliance on which the respective application (destination application) is implemented is secure or nonsecure. A secure appliance is then one on which a trader module is active that has connected itself to the memory module from a remote network address (for example using a URL or another link) and has registered itself in said memory module.

In principle, the method according to an embodiment of the invention can be used inside or outside an automated, medical workflow, as a result of which it is also possible for copy and paste operations to be handled via the clipboard. Hence, selected workflow steps can be made more secure. When a clinical diagnosis report is created, the elements of the patient identification (name, date of birth, sex, ID number in the hospital) or the images of the patient, for example, are intended—in a nonsecure environment—to be automatically transferred from an application to the report by way of clipboard copy and paste. In a nonsecure environment, security-critical access to the clipboard could tap off these PHI data from the clipboard from the side.

In contrast to macro recorders from the prior art, which record the flow of the executed commands within the application, all command sequences are prescribed in the case of this invention—particularly for security reasons. Nevertheless, it becomes possible to transfer contents from one application to another (including across computers). A copy and paste command always targets the currently selected data: for "copy", data in the application are selected, and for "paste" the data from the clipboard are 'selected'. The functional execution of the data transport to the application or from it is then effected using customary commands, such as load, store, save, which are provided generically (independently of application) by a framework within the application. A copy and paste command can therefore be executed securely and absolutely on a situation and data specific basis.

In principle, different deployments of the method according to an embodiment of the invention are possible. Preference is given to single user deployment, in which one user is logged in on an appliance in a particular time phase.

The transfer method according to an embodiment of the invention therefore ensures that the PHI data to be transferred can always be transferred from a source application to the destination application, while observing the security provisions beyond the application boundaries.

If the destination application is a nonsecure application, the destination application—so to speak: as usual—uses the detected key to access the local clipboard (or pasteboard) and receives the anonymized image data record that is associated with the key. Hence, only anonymized data records are presented on the destination appliance (as a default setting). Hence, automatically only the anonymized image data are pasted. In this case, the destination application cannot evaluate the detected key and use it for decryption, as a result of which only anonymized (or encrypted) data records can be pasted on the destination application.

If the destination application is a secure application, the trader module is activated. The trader module uses the detected key to automatically access the encrypted PHI data that are respectively associated with the key in order to decrypt said PHI data and to paste them as plain text (in unencrypted form) in the destination application.

The Customary Procedure Will be Described Briefly Below:

The user has loaded patient data in a medical application and, by way of example, selects one of the or else a plurality of patient images and executes the 'Clipboard Copy' function. The medical application now stores each image twice, both the encrypted original image and an anonymized version (preferably created on the fly) of the same image that no longer contains a patient identity. The encryption is performed using the key of the user from the provided PKI infrastructure. The user is explicitly identifiable by way of this key on any appliance or device. The encrypted original image can be read again only by this user and only in secure destination applications on these devices. Therefore, both images are stored with the user key, which also serves as a primary search key, in order to find the images of this user on any device. The token per image allows the user to copy a plurality of images simultaneously, and to select arbitrary images from a plurality of stored (buffer-stored) images for the paste command. The image pairs are stored repeatedly. The clipboard of the local machine and a secure repository (that may be cloud-based), namely the memory module, are used. All devices on which the user is logged in connect to one another or have already connected to the cloud repository and are notified when image pairs are stored in the repository and/or on the clipboard on one of these devices for this user. On the basis of this notification, all devices automatically fill the local clipboard with the new image pairs (the data records being stored with the key and a token). All clipboards on all devices then have the same data.

If the user now changes to a nonsecure application on another or the same device and executes a paste command, the nonsecure application—as usual—accesses the clipboard, possibly even ignores the key and the tokens (because it usually cannot evaluate both) and, in the simplest case, will paste only the first anonymized image.

If the user changes to a secure application on another or the same device and executes a paste command, the secure application reads the user key on the local machine, uses it to access the clipboard, finds the key and the tokens and uses the key to search the clipboard and the memory module or the cloud repository, using this key, for data in order to decrypt the data thus found and to display all original images to the user for selection. The user selects images and the application pastes the selected original images (e.g. into a secure clinical examination application). As a security measure, the clipboard and the cloud repository are erased under time control (e.g. by way of memory erasure operations, known as garbage collection mechanism).

An essential feature is that automatic production and storage of the date convolute (as described above: for the data pair with and without PHI data) in the nonsecure copy and paste environment are effected by the additional new components in the secure applications (these components anonymize the data and transfer the data with and without PHI to the Secu-SnapTrader).

An important aspect can also be seen in that these medical data are copied and distributed to both all local clipboards and the memory module or the cloud repository by way of the additional and autonomous infrastructure components to the trader module (also called SecuSnapTrader) and to the memory module (also called: SecuSnapStore). This allows copy and paste across appliances, specifically regardless of the type of the hardware or the type of the operating system (and without additional details from the user, e.g. about the destination appliance). It is advantageous that both secure and nonsecure applications are supported automatically. This occurs transparently for the user and technically transparently for arbitrary nonsecure applications.

According to one preferred embodiment of the invention, a token is associated with a respective entity of an image data record as an identification feature, as a result of which a plurality of image data records or portions thereof can also be accumulated and gathered on the clipboard and/or in the memory module and as a result of which a multipaste command can also be executed. In other words, a user can also execute paste commands repeatedly in succession and each time select the relevant image data records from the available ones. The token is therefore used as an access means and an indicator and is ultimately intended for the user, as a result of which all of the tokens form a type of "structured list of contents" for the available image data records on the pasteboard and/or in the memory module. This also allows sequentially stored (copied) PHI contents to be selected or jointly "pasted" in the destination application.

According to a more broadly preferred embodiment of the invention, the key is simultaneously used for two different functions: firstly for encrypting the image data record and secondly for identifying an image data record or as a primary search key in a data structure for the image data records (e.g. on the clipboard or pasteboard or in the memory module).

According to a more broadly preferred embodiment of the invention, the memory module and/or the clipboard is/are used to store an association entity, at least comprising the key, the anonymized image data record associated with the respective key and the encrypted image data record associated with the respective key. The PHI data in plain text are not stored on the clipboard and on the memory module, as a result of which it is possible to ensure that the PHI data to be protected do not leave the respective machine boundary (verified as secure).

According to a more broadly preferred embodiment of the invention, all appliances on which the user is logged in receive a message that image data records have been stored and are therefore available for the user on the clipboard and/or in the memory module. This message passes from the trader to the memory module and to all other traders on the other appliances. The other traders on the other appliances had registered for the use of the memory module on the trader (so to speak in parallel with or beside the memory module) after the user had logged in. Hence, the trader beside the memory module can use this memory module itself to store the call address for the traders on the other appliances and to read it again for sending messages. In this case, the call address for the other traders is also kept available with the key as a primary key in the memory module. This aspect of the invention provides a distributed clipboard mechanism having remote access and notification and automatic distribution of the clipboard data.

According to a more broadly preferred embodiment of the invention, a trader is installed for a respective application appliance on which the source application and/or the destination application are implemented.

A customary procedure for the transfer method takes the following form: when a trader that is installed on an appliance receives a message that image data records have been stored and are therefore available for the user on the clipboard and/or in the memory module, the trader reads the anonymized image data records from the memory module and stores them on the local clipboard on the appliance. A nonsecure destination application reads the anonymized image data records in the same way as if the nonsecure destination application and the source application were situated on the same appliance.

By way of development and optimization, all image data can be kept locally on the clipboard in order to speed up the access to the image data by a secure destination application.

A fundamental advantage of an embodiment of the method described above can be seen in that a transfer function can be used to serve both secure and nonsecure applications in equal measure. Furthermore, the transfer function can also be applied across machine boundaries (cross-device).

It is likewise within the scope of embodiments of the invention for the aforementioned steps of the method not necessarily to be executed in the order described above. Alternatively, it is also possible, by way of example, for a plurality of copy commands to be executed first followed by one or more paste commands on the destination application. In a further embodiment, the method steps of copying and pasting the image data may be interleaved, as a result of which detection of a paste command immediately prompts the appearance and possible activation of a window on the monitor of the destination system that can be used to selectively choose one or more of the available image data items for pasting. This window can be activated either for one image or for a group of images (e.g. a series of images from an examination)—for example by virtue of a mouse click.

Furthermore, it is possible for individual sections of the method described above to be produced as individual saleable units and for the remaining sections of the method to be produced as other saleable units. Hence, the method according to an embodiment of the invention can be executed as a distributed system on different computer-based entities (e.g. client-server entities). By way of example, it is thus possible for the trader module for its part to comprise different sub-modules that are implemented partly on the source application, partly on the destination application and/or partly on other computer-based entities.

Furthermore, an embodiment is directed to a computer program product.

Furthermore, an embodiment is directed to a computer program that comprises computer instructions. The computer instructions may be stored directly on a memory in a computer or can be loaded via a network and comprise commands that the computer can read and that are intended for executing the method described above when the commands are executed on the computer. The computer program may also be stored on a storage medium or it can be downloaded from a server via an appropriate network.

Figure 1:
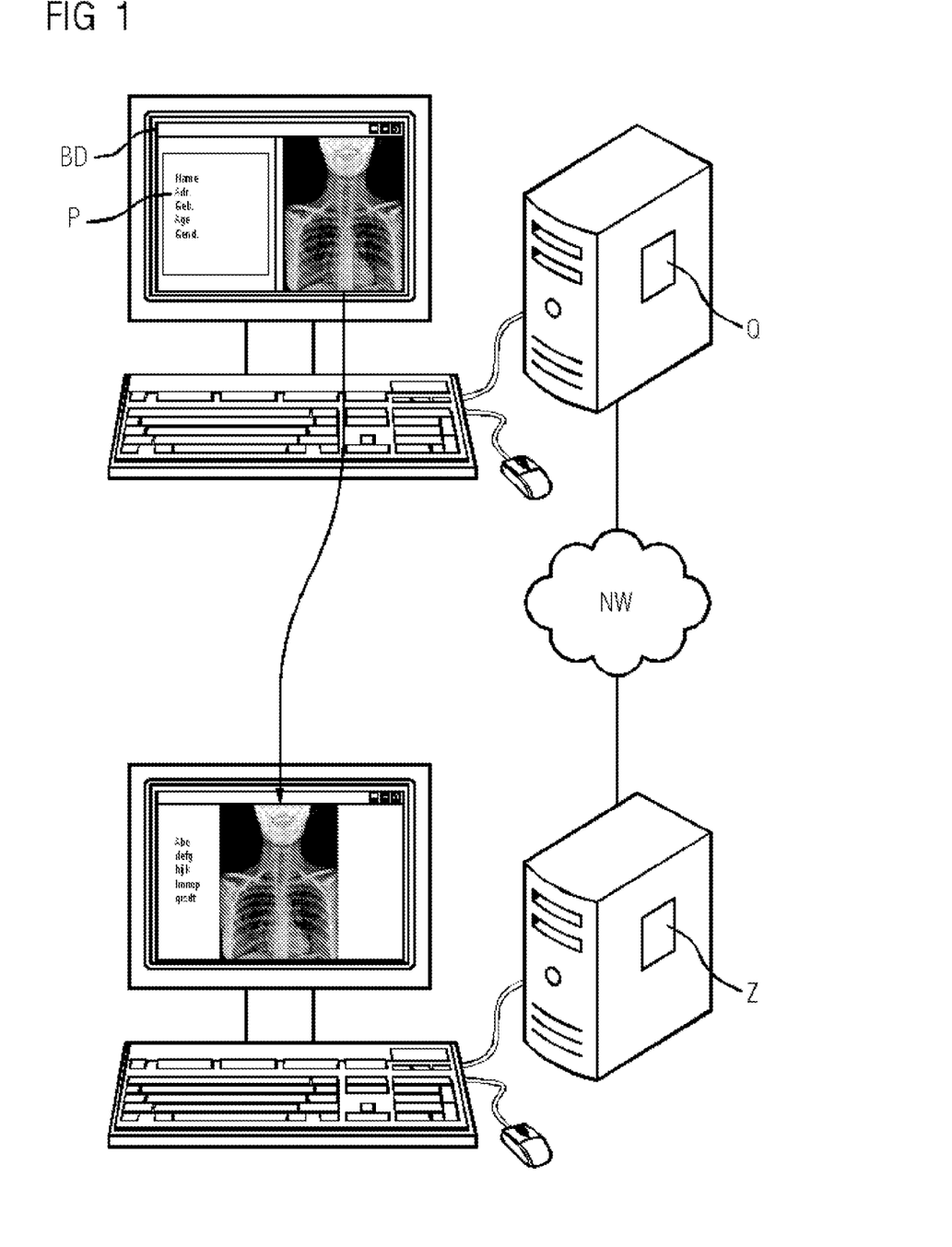
FIG. 1 shows a basic illustration for a copy and paste command.

As FIG. 1 shows, image data are intended to be transferred from a source application Q to a destination application Z. The source application Q runs on a first appliance and the destination application Z runs on a second, the appliances G being in data interchange via a network.

To that extent, this also applies to known copy and paste commands. In contrast to known methods, at least one embodiment of the invention is distinguished in that the data to be transferred comprise image data BD and furthermore data that require secrecy, are to be protected or are to be secured, what is known as protected health information, PHI data for short, which are denoted by the reference symbol P in the figures. The PHI data may be in different formats, preferably in a DICOM format, and usually comprise image data relating to a health condition of a patient (diagnosis, findings, therapy-related data records, cost-unit-related data records, etc.). The PHI data P always have a medical content.

If data records with PHI sections P now need to be copied and pasted at another location, the previous copy and paste functions that are usually provided by the operating system cannot be used because the security criteria (protection of PHI data) cannot automatically be observed.

This is the starting point for at least one embodiment of the invention, which provides an IT infrastructure that automatically allows secure execution of a copy and paste command even beyond application or appliance boundaries.

In principle, the transfer method according to at least one embodiment of the invention for image data records BD with PHI sections P can serve both secure and nonsecure destination applications. A destination application is deemed "secure" when it is either the same application as the source application Q or is situated in the same information technology environment as the source application Q or is registered in the transfer system and hence has a connection to a trader module Tr and/or to a memory module S. The trader module Tr knows the address or URL of the memory module S by virtue of configuration. When the trader module Tr is started, the trader module Tr uses the URL of the memory module S to access the memory module S and transfers its own URL, that is to say the URL of the trader module Tr, to said memory module. In addition, the trader module Tr transfers the key—key—of the current user to the memory module S. In the case of de-registration, the trader module Tr erases its URL in the memory module S. The trader module Tr can later access the memory module S in order to transmit data for a key—key. The memory module S will then transmit these data for all registered other trader modules Tr if these trader modules Tr had registered using the same key—key.

All other destination applications Z are deemed prima facie "nonsecure".

When the transfer method according to at least one embodiment of the invention is executed for PHI image data records BD, it is now automatically detected whether the destination application Z is secure or nonsecure.

Figure 2:
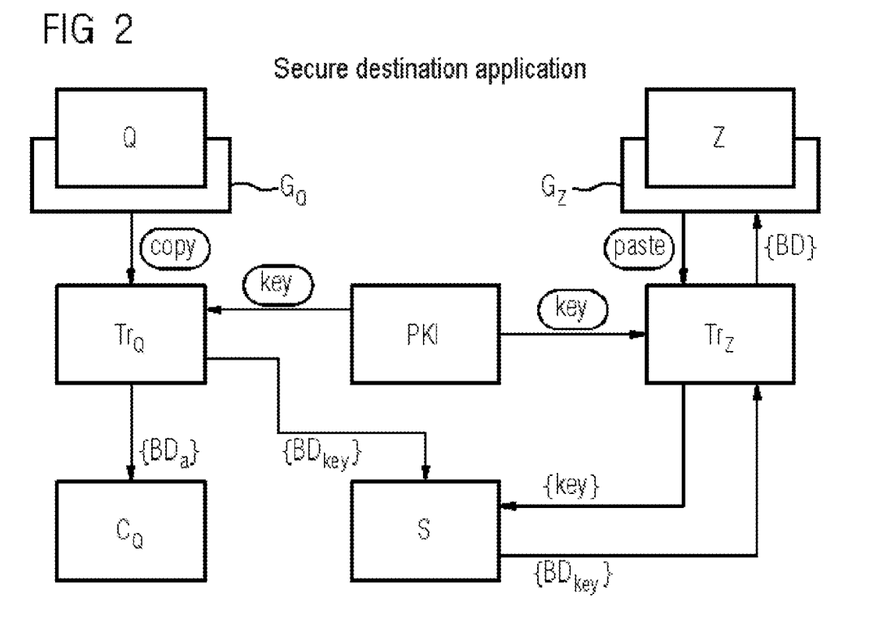
FIG. 2 shows a schematic illustration for the execution of a copy and paste command for a secure destination application according to an example embodiment of the invention

In the event of it being a secure destination application Z, an example embodiment is shown in FIG. 2. The system has detected that the destination application Z is deemed secure. On the source application, source application Q, that is executed on an appliance GQ, a copy command is detected and is forwarded to a trader module Tr, which in this case is associated with the source application Q and therefore bears the reference symbol TrQ. The source application Q transfers the image data BD to be copied likewise to the trader module TrQ. The trader module TrQ can then detect a key—key— associated with the appliance GQ or with the user or the application, source application Q, from a central PKI entity (public key infrastructure) PKI. The key—key—is used for encrypting the image data record BD to be pasted. Furthermore, the Tr creates an anonymized image data record BDa that no longer contains any contents identifying the patient.

According to at least one embodiment of the invention, the image data BD to be transferred are thus taken as a basis for creating a data convolute, comprising an encrypted image data record BDkey and an anonymized image data record BDa. Hence, three entities of the original image data record BD arise:

1. the original image data record BD
2. the anonymized image data record $BD_a$ and
3. the encrypted image data record $BD_{key}$.

In one preferred embodiment, the anonymized image data record BDa is transferred to a (usually) local clipboard C (in this case, as shown in FIG. 2: CQ, because the clipboard is associated with the source application Q) and the encrypted image data record BDkey is transferred to a memory module S.

The memory module S may be in the form of a server and can be provided as a cloud-based service in a network architecture. The same applies to the trader module Tr.

As soon as a paste command is now detected on the destination application Z, said paste command is forwarded to the (likewise preferably local) trader module Tr. The trader module Tr can then read the associated key—key—from the PKI entity PKI and use the key—key—to access the memory module S.

A feature of at least one embodiment of this invention can now be seen in that the key simultaneously performs two functions:

1. it is used for encryption and decryption and
2. it is simultaneously also used as a primary key for accessing a particular data record in the memories (memory module S, clipboard C), that is to say as an identifier or accessor.

The trader module Tr (in this case TrZ) uses the key— key—to find the encrypted image data record BDkey intended for the destination application. This image data record can then be decrypted on the trader module Tr (or in the application Z) using the key—key—and provided as plain text (that is to say in decrypted form) on the destination application Z. Preferably, the decrypted image data record contains the PHI information. It may be preset that the decrypted image data record matches the original image data record BD. Otherwise, it may be set that particular sections are not pasted as well or that additional sections are pasted as well. In this case, the decrypted image data record that is pasted on the destination application Z contains meta information, e.g. about the source application Q, about the time of the copy command, the time of the paste command and/or further data and/or a flag (highlighting) for the PHI data P.

Figure 3:
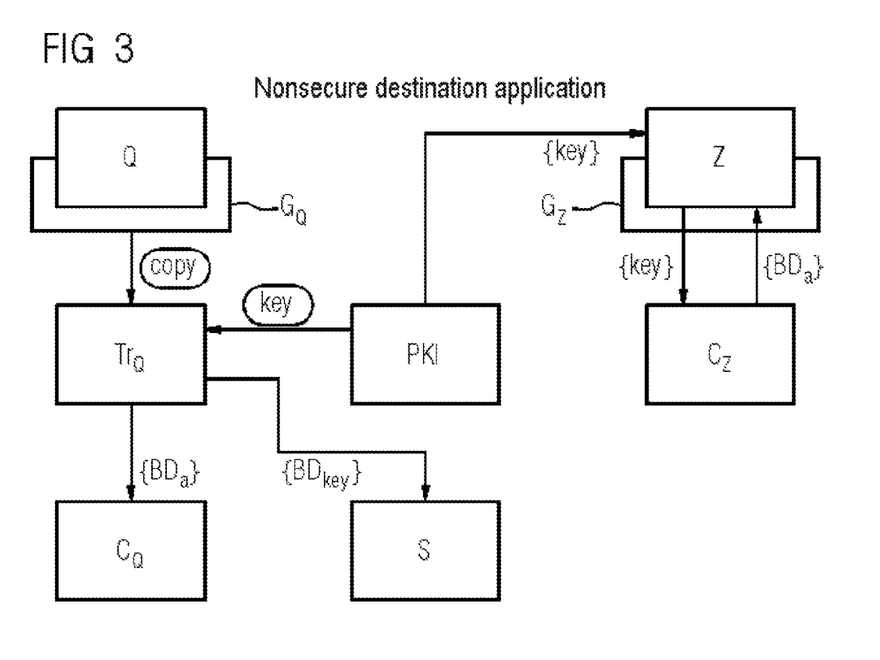
FIG. 3 shows a schematic illustration for the execution of a copy and paste command for a nonsecure destination application according to an example embodiment of the invention

In the event of the destination application Z having been evaluated as a nonsecure application, the procedure in the transfer method is explained with reference to FIG. 3. The method steps that are executed in connection with the copy command match those from the scenario for the secure application (see above and shown on the left-hand side in FIG. 3). The paste operation differs, however. Detection of a paste command on the destination application Z prompts detection of the key—key—which is then used to access the (usually: local) clipboard C (in this case CZ) in order to access the anonymized image data record BDa associated with the key—key—and to transfer it to the destination application Z or to paste it to the position determined by the cursor.

A fundamental feature is that the format of the files on which the copy and paste commands are intended to be executed may be different. Thus, the source application Q may be based on a DICOM format and the destination application Z may be based on a .txt or .ppt format or another format, which does not necessarily need to be designed for image contents.

Figure 4:
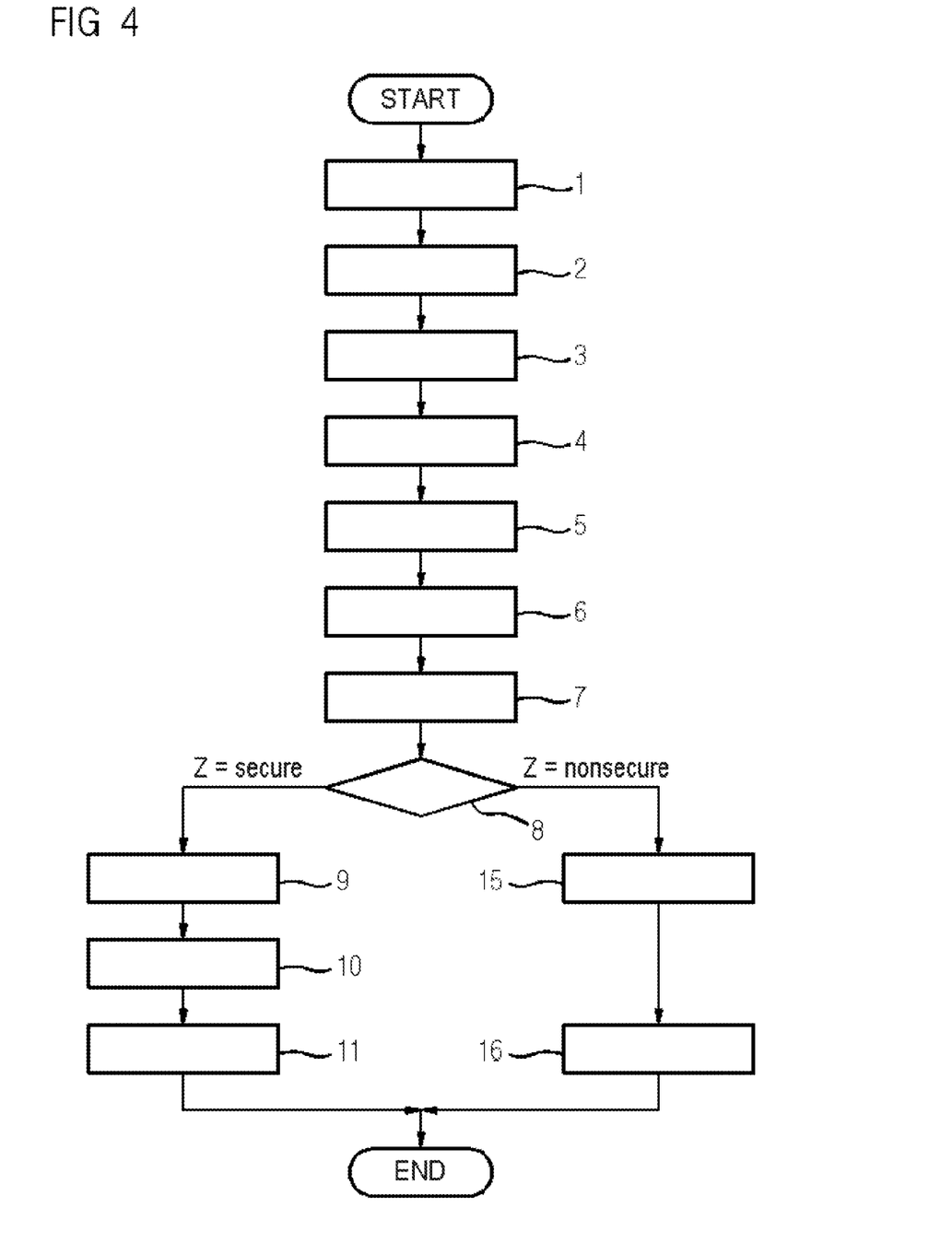
FIG. 4 shows a flowchart according to a preferred procedure for a method according to an example embodiment of the invention.

With reference to FIG. 4, the procedure in the transfer method according to a preferred embodiment is described below.

After the method is started, the copy command is detected in step 1. This takes place on the source application Q. Next, the key—key—is detected in step 2. This can be executed on the source application Q or on the trader module Tr. In step 3, the data convolute is created, comprising 1. the anonymized image data record BDa and 2. the encrypted image data record BDkey. In step 4, at least the anonymized image data record BDa is forwarded to the clipboard C, and in step 5 the encrypted image data record BDkey is forwarded to the memory module S, and buffer-stored therein. It is also possible for a plurality of image data records to be stored in the memories C, S sequentially that are identifiable by means of a token T. It is also possible for the entire, generated data convolute (with anonymized image data record BDa and encrypted image data record BDkey) to be stored on the clipboard C and/or on the mirror module S. Steps 3 to 5 are preferably executed on the trader module Tr. However, it is also possible for individual method steps to be relocated to the source application Q and/or other entities. In step 6, a paste command is detected on the destination application Z. In step 7, the key—key—is detected. In step 8, an evaluation is performed to determine whether the destination application Z is of "secure" (shown on the left in FIG. 4) or "nonsecure" (shown on the right) type.

If it is a secure destination application Z, the paste command is forwarded to the trader or the trader module Tr in step 9, as a result of which the latter can use the detected key— key—in step 10 to access the memory module S and/or the clipboard C in order to retrieve the encrypted image data record BDkey associated with the key—key—and in order to decrypt it in step 11, likewise using the key—key—, and in order then to paste the result (the original image data BD) into the destination application Z. The method then ends or can be continued again, e.g. for other image data records BD.

If it is a nonsecure destination application Z, the destination application Z uses the detected key—key—in step 15 to access the memory module S in order to retrieve the anonymized image data record BDa from the clipboard C and to forward it in step 16 to the destination application Z for the purpose of pasting. The method can then likewise end or be continued again.

Finally, it should be pointed out that the above description of the invention with the example embodiments is in principle not intended to be understood to be restrictive in respect of a particular physical implementation of the invention. It is thus particularly clear to a person skilled in the art that embodiments of the invention is in principle not limited to a particular data format (e.g. DICOM image data) but rather can likewise be used for other data formats (text data, etc.). Furthermore, it is also not absolutely necessary to resort to cloud-based communication technology. By way of example, proprietary protocols for a process communication can also be used in this case. Furthermore, embodiments of the invention may be implemented partly or completely in software and/or in hardware. Furthermore, the method according to embodiments of the invention or the transfer system can also be implemented in a manner distributed over a plurality of physical products, comprising computer program products. Hence, it is possible to implement a portion of the control of the transfer on the source system Q and a remaining portion of the control on the destination system Z, and vice versa.

What is claimed is:

1. A method for providing a transfer function for security-critical medical image data records with protected health information (PHI) sections from a source application to a destination application, wherein the method can simultaneously serve secure and nonsecure destination applications, and wherein the method accesses a public key infrastructure (PKI) that provides a user-specific key for each user, the method comprising:
    forwarding, to a trader module on a processor of a transfer system for security-critical medical image data records, an image data record and an anonymized image data record, following detection of a copy command for the image data record in the source application, the image data record including protected health information (PHI) and image data representing an image, and the anonymized image data record including the image data representing the image;
    creating, by the trader module on the processor, at least two data convolutes for the image data record, a first of the at least two data convolutes including the anonymized image data record and a second of the at least two data convolutes including an encrypted image data record;
    forwarding, by the trader module on the processor, at least the anonymized image data record to a clipboard;
    forwarding, by the trader module on the processor, at least the encrypted image data record to a memory module, the memory module being configured to store the encrypted image data record and an association entity for a user-specific key associated with the encrypted image data record; and
    detecting, by the trader module on the processor following detection of a paste command for the image data record in the destination application, the user-specific key and whether the destination application is registered as a secure or nonsecure application;
    wherein, if the destination application is a nonsecure application, the method further includes,
        accessing, by the trader module on the processor, the clipboard via the destination application in order to access the anonymized image data record associated with the detected user-specific key and to present the anonymized image data record associated with the detected user-specific key on the destination application; and
    wherein, if the destination application is a secure application, the method further includes,
        forwarding the paste command from the destination application to the trader module,
        accessing, by the trader module on the processor using the detected user-specific key, the memory module in order to access the encrypted image data record associated with the detected user-specific key,
        decrypting, by the trader module on the processor using the detected user-specific key, the encrypted image data record associated with the detected user-specific key, and
        providing, by the trader module on the processor, the decrypted image data record on the destination application.

2. The method of claim 1, wherein a token is associated with a respective entity of an image data record as an identification feature, as a result of which a plurality of image data records or portions thereof are gatherable at least one of on the clipboard and in the memory module, and as a result of which a multipaste command is executable.

3. The method of claim 1, wherein the user-specific key is simultaneously used for two different functions.

4. The method of claim 1, wherein the association entity includes at least the user-specific key.

5. The method of claim 1, further comprising:
    receiving, at all appliances on which the user is logged in, a message that image data records have been stored for the user at least one of on the clipboard and in the memory module.

6. The method of claim 1, wherein a trader module is installed for a respective appliance on which at least one of the source application and the destination application are implemented.

7. A non-transitory computer-readable storage medium including computer program code that when executed by a computer or a computer-based appliance causes the computer or computer-based appliance to perform a method for providing a transfer function for security-critical medical image data records with protected health information (PHI) sections from a source application to a destination application, wherein the method can simultaneously serve secure and nonsecure destination applications, and wherein the method accesses a public key infrastructure (PKI) that provides a user-specific key for each user, the method comprising:
    forwarding, to a trader module, an image data record and an anonymized image data record, following detection of a copy command for the image data record in the source application, the image data record including protected health information (PHI) and image data representing an image, and the anonymized image data record including the image data representing the image;
    creating at least two data convolutes for the image data record, a first of the at least two data convolutes including the anonymized image data record and a second of the at least two data convolutes including an encrypted image data record;
    forwarding at least the anonymized image data record to a clipboard;
    forwarding at least the encrypted image data record to a memory module, the memory module being configured to store the encrypted image data record and an association entity for a user-specific key associated with the encrypted image data record; and
    detecting, following detection of a paste command for the image data record in the destination application, the user-specific key and whether the destination application is registered as a secure or nonsecure application;
    wherein, if the destination application is a nonsecure application, the method further includes,
        accessing the clipboard via the destination application in order to access the anonymized image data record associated with the detected user-specific key and to present the anonymized image data record associated with the detected user-specific key on the destination application; and wherein, if the destination application is a secure application, the method further includes, forwarding the paste command from the destination application to the trader module, accessing, using the detected user-specific key, the memory module in order to access the encrypted image data record associated with the detected user-specific key, decrypting, using the detected user-specific key, the encrypted image data record associated with the detected user-specific key, and providing the decrypted image data record on the destination application.

8. A transfer system for security-critical medical image data records with protected health information (PHI) sections from a source application to a destination application, the system comprising:

a processor configured to, execute a source application in which at least one copy command for at least one image data record is detectable, the at least one image data record including protected health information (PHI) and image data representing an image, and execute a destination application in which at least one paste command is detectable;

a PKI infrastructure configured to provide a user-specific key for each user;

a trader module configured to generate an anonymized image data record and an encrypted image data record for each image data record, the anonymized image data record including the image data representing the image;

a memory configured to store at least the encrypted image data record; and a clipboard configured to store at least the anonymized image data record;

wherein the transfer system is configured to simultaneously serve secure and nonsecure destination applications;

wherein, in the case of a nonsecure destination application, the trader module is configured to, access the clipboard to detect the anonymized image data record associated with a detected user-specific key, and present the anonymized image data record associated with the detected user-specific key on the destination application; and wherein, in the case of a secure destination application, the trader module is configured to, access, using the detected user-specific key, the memory module to obtain the encrypted image data record associated with the detected user-specific key, decrypt the encrypted image data record associated with the detected user-specific key using the detected user-specific key, and paste the decrypted image data record on the destination application.

9. The method of claim 3, wherein the detected user-specific key is simultaneously used to encrypt the image data record and to identify an image data record.

10. The method of claim 4, wherein the association entity further includes the anonymized image data record associated with the user-specific key and the encrypted image data record associated with the user-specific key.

11. The method of claim 2, wherein the user-specific key is simultaneously used for two different functions.

12. The method of claim 2, wherein the association entity includes at least the user-specific key.

13. The method of claim 2, further comprising:

receiving, at all appliances on which the user is logged in, a message that image data records have been stored for the user at least one of on the clipboard and in the memory module.

14. The method of claim 2, wherein a trader module is installed for a respective appliance on which at least one of the source application and the destination application are implemented.

15. The non-transitory computer-readable storage medium of claim 7, wherein a token is associated with a respective entity of an image data record as an identification feature, as a result of which a plurality of image data records or portions thereof are gatherable at least one of on the clipboard and in the memory module, and as a result of which a multipaste command is executable.

* * * * *